United States Patent
Frey et al.

(10) Patent No.: US 9,193,644 B2
(45) Date of Patent: Nov. 24, 2015

(54) PROCESS FOR SELECTIVELY DEALKYLATING AROMATIC COMPOUNDS

(71) Applicant: UOP LLC, Des Plaines, IL (US)

(72) Inventors: Stanley J. Frey, Palatine, IL (US); Paul T. Barger, Arlington Heights, IL (US); Maureen L. Bricker, Buffalo Grove, IL (US); John Q. Chen, Glenview, IL (US); Peter K. Coughlin, Mundelein, IL (US); James A. Johnson, Burr Ridge, IL (US); Joseph A. Kocal, Glenview, IL (US); Matthew Lippmann, Chicago, IL (US); Vasant P. Thakkar, Elk Grove Village, IL (US); Kurt M. Vanden Bussche, Lake in the Hills, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/718,877

(22) Filed: May 21, 2015

(65) Prior Publication Data
US 2015/0251971 A1 Sep. 10, 2015

Related U.S. Application Data

(62) Division of application No. 14/467,723, filed on Aug. 25, 2014, now Pat. No. 9,067,853.

(60) Provisional application No. 61/905,924, filed on Nov. 19, 2013.

(51) Int. Cl.
*C07C 4/14* (2006.01)
*C10G 47/04* (2006.01)
*C10G 47/14* (2006.01)
*C10G 47/18* (2006.01)
*C10G 47/20* (2006.01)
*C10G 45/04* (2006.01)
*C07C 4/18* (2006.01)
*C10G 65/12* (2006.01)
*C10B 53/00* (2006.01)

(52) U.S. Cl.
CPC . *C07C 4/18* (2013.01); *C10B 53/00* (2013.01); *C10G 65/12* (2013.01); *C07C 2529/06* (2013.01)

(58) Field of Classification Search
USPC .............. 585/319, 320, 489; 208/107, 208 R, 208/251 R, 254 R
See application file for complete search history.

(56) References Cited

U.S. PATENT DOCUMENTS 3,623,973 A * 11/1971 Tarhan ............................ 208/60

* cited by examiner

Primary Examiner — Thuan D Dang

(57) ABSTRACT

A process for selectively dealkylating aromatic compounds includes providing a coal tar stream comprising aromatic compounds and hydrotreating the coal tar stream to reduce a concentration of one or more of organic sulfur, nitrogen, and oxygen in the coal tar stream, and to hydrogenate at least a portion of the aromatic compounds in the coal tar stream. The process further includes hydrocracking the hydrotreated coal tar stream to further hydrogenate the aromatic compounds and to crack at least one ring of multi-ring aromatic compounds to form single-ring aromatic compounds. The single-ring aromatic compounds present in the hydrocracked stream are then dealkylated to remove alkyl groups containing two or more carbon atoms.

7 Claims, 2 Drawing Sheets

PROCESS FOR SELECTIVELY DEALKYLATING AROMATIC COMPOUNDS

CROSS-REFERENCE TO RELATED APPLICATIONS

This application is a Division of copending application Ser. No. 14/467,723 filed Aug. 25, 2014, which application claims priority from Provisional Application No. 61/905,924 filed Nov. 19, 2013, the contents of which are hereby incorporated by reference.

BACKGROUND OF THE INVENTION

Many different types of chemicals are produced from the processing of petroleum. However, petroleum is becoming more expensive because of increased demand in recent decades.

Therefore, attempts have been made to provide alternative sources for the starting materials for manufacturing chemicals. Attention is now being focused on producing liquid hydrocarbons from solid carbonaceous materials, such as coal, which is available in large quantities in countries such as the United States and China.

Pyrolysis of coal produces coke and coal tar. The coke-making or "coking" process consists of heating the material in closed vessels in the absence of oxygen to very high temperatures. Coke is a porous but hard residue that is mostly carbon and inorganic ash, which may be used in making steel.

Coal tar is the volatile material that is driven off during heating, and it comprises a mixture of a number of hydrocarbon compounds. It can be separated to yield a variety of organic compounds, such as benzene, toluene, xylene, naphthalene, anthracene, and phenanthrene. These organic compounds can be used to make numerous products, for example, dyes, drugs, explosives, flavorings, perfumes, preservatives, synthetic resins, and paints and stains. The residual pitch left from the separation is used for paving, roofing, waterproofing, and insulation.

Coal tar is useful for producing aromatic and alkylaromatic compounds such as benzene, toluene, and xylenes, which are valuable as products or intermediates. Thus, there is a need for a process for producing single-ring aromatic compounds and for removing undesirable alkyl groups from those compounds.

SUMMARY OF THE INVENTION

In a first aspect, a process for selectively dealkylating aromatic compounds includes providing a coal tar stream comprising aromatic compounds and hydrotreating the coal tar stream to reduce a concentration of one or more of organic sulfur, nitrogen, and oxygen in the coal tar stream, and to hydrogenate at least a portion of the aromatic compounds in the coal tar stream. The process further includes hydrocracking the hydrotreated coal tar stream to further hydrogenate the aromatic compounds and to crack at least one ring of multi-ring aromatic compounds to form single-ring aromatic compounds. The single-ring aromatic compounds present in the hydrocracked stream are then dealkylated to remove alkyl groups containing two or more carbon atoms.

In another aspect, a process for selectively dealkylating aromatic compounds includes pyrolyzing a coal feed into a coke stream and a coal tar stream comprising aromatic compounds. The coal tar stream is hydrotreated to reduce a concentration of one or more of organic sulfur, nitrogen, and oxygen in the coal tar stream, and to hydrogenate at least a portion of the aromatic compounds in the coal tar stream. The process further includes hydrocracking the hydrotreated coal tar stream to further hydrogenate the aromatic compounds and to crack at least one ring of multi-ring aromatic compounds to form single-ring aromatic compounds, and dealkylating the single-ring aromatic compounds in the hydrocracked coal tar stream to remove alkyl groups containing two or more carbon atoms.

DETAILED DESCRIPTION OF THE INVENTION

Figure 1:
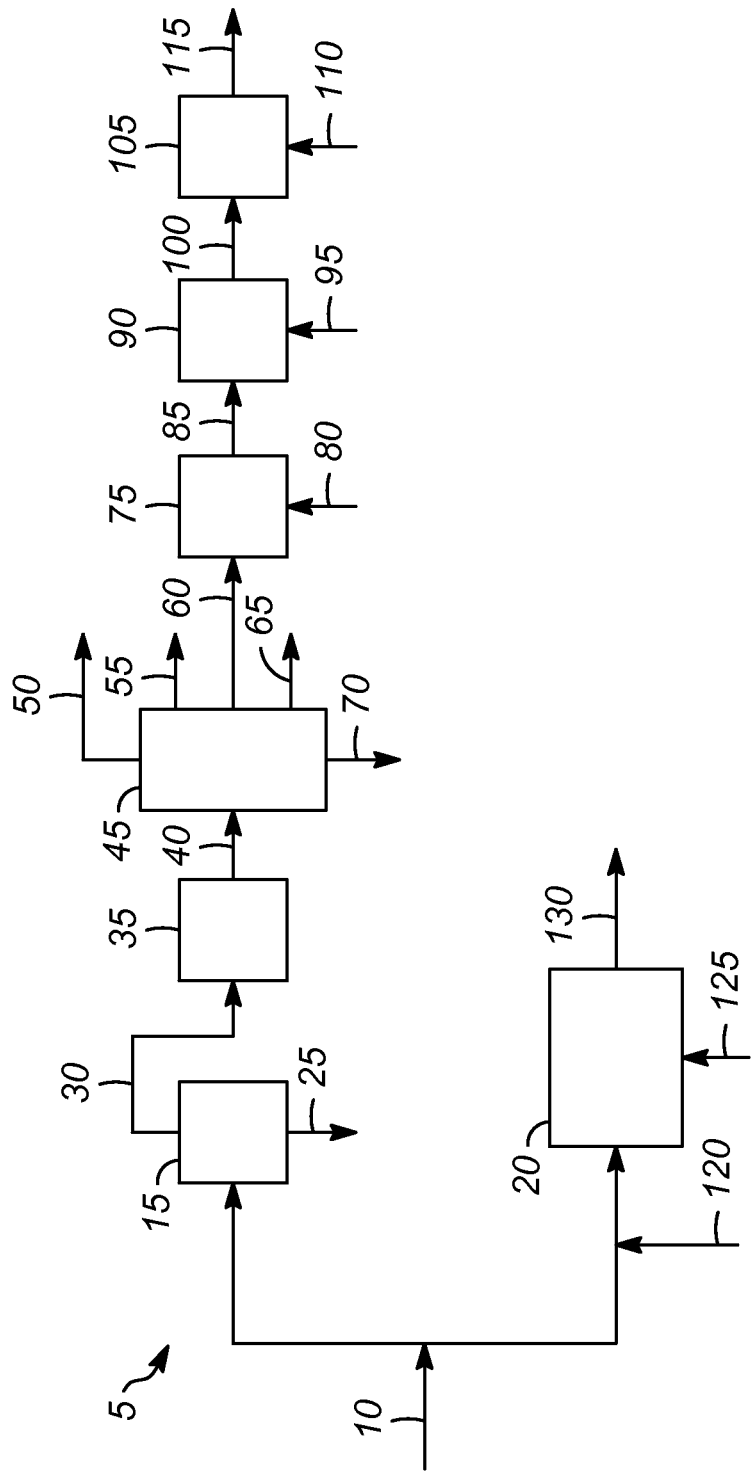
FIG. 1 is an illustration of one embodiment of the process of the present invention for dealkylating aromatic compounds.

FIG. 1 shows one embodiment of a coal conversion process 5 of the present invention. A coal feed 10 can be sent to a pyrolyzing zone 15, such as a coking oven, or a gasification zone 20. Alternatively, the coal feed 10 can be split into two parts and sent to both the pyrolyzing zone 15 and the gasification zone 20.

In the pyrolyzing zone 15, the coal feed 10 is heated to a high temperature, e.g., up to about 2,000° C. (3,600° F.), in the absence of oxygen to drive off the volatile components. Coking produces a coke stream 25 and a coal tar stream 30. The coke stream 25 can be used in other processes, such as the manufacture of steel.

The coal tar stream 30 which comprises the volatile components from the coking process can be sent to an optional contamination removal zone 35, if desired.

The contaminant removal zone 35 for removing one or more contaminants from the coal tar stream or another process stream may be located at various positions along the process depending on the impact of the particular contaminant on the product or process and the reason for the contaminant's removal, as described further below. For example, the contaminant removal zone 35 can be positioned upstream of a separation zone 45. Some contaminants have been identified to interfere with a downstream processing step or hydrocarbon conversion process, in which case the contaminant removal zone 35 may be positioned upstream of the separation zone 45 or between the separation zone 45 and the particular downstream processing step at issue. Still other contaminants have been identified that should be removed to meet particular product specifications. Where it is desired to remove multiple contaminants from the hydrocarbon or process stream, various contaminant removal zones 35 may be positioned at different locations along the process. In still other approaches, a contaminant removal zone 35 may overlap or be integrated with another process within the system, in which case the contaminant may be removed during another portion of the process, including, but not limited to the separation zone 45 or the downstream hydrocarbon conversion zone. This may be accomplished with or without modification to these particular zones, reactors or processes. While the contaminant removal zone 35 is often positioned downstream of the hydrocarbon conversion reactor, it should be understood that the contaminant removal zone 35 in accordance herewith may be positioned upstream of the separation zone, between the separation zone and the hydrocarbon conversion zone, or downstream of the hydrocarbon conversion zone 35 or along other streams within the process stream, such as, for example, a carrier fluid stream, a fuel stream, an oxygen source stream, or any streams used in the systems and the processes described herein. The contaminant concentration is controlled by removing at least a portion of the contaminant from the coal tar stream 30. As used herein, the term "removing" may refer to actual removal, for example by adsorption, absorption, or membrane separation, or it may refer to conversion of the contaminant to a more tolerable compound, or both.

The decontaminated coal tar feed 40 is sent to a separation zone 45 where it is separated into two or more fractions 50, 55, 60, 65, 70. Coal tar comprises a complex mixture of heterocyclic aromatic compounds and their derivatives with a wide range of initial boiling points. The number of fractions and the components in the various fractions can be varied as is well known in the art. A typical separation process involves separating the coal tar into four to six streams. For example, there can be a fraction comprising $NH_3$, CO, and light hydrocarbons, a light oil fraction with boiling points between 0° C. and 180° C., a middle oil fraction with boiling points between 180° C. to 230° C., a heavy oil fraction with boiling points between 230 to 270° C., an anthracene oil fraction with boiling points between 270° C. to 350° C., and pitch.

The light oil fraction contains compounds such as benzenes, toluenes, xylenes, naphtha, coumarone-indene, dicyclopentadiene, pyridine, and picolines. The middle oil fraction contains compounds such as phenols, cresols and cresylic acids, xylenols, naphthalene, high boiling tar acids, and high boiling tar bases. The heavy oil fraction contains benzene absorbing oil and creosotes. The anthracene oil fraction contains anthracene. Pitch is the residue of the coal tar distillation containing primarily aromatic hydrocarbons and heterocyclic compounds.

As illustrated, the coal tar feed 40 is separated into a gas fraction 50 containing gases such as $NH_3$ and CO as well as light hydrocarbons, such as ethane, hydrocarbon fractions 55, 60, and 65 having different boiling point ranges, and a pitch fraction 70. Suitable separation processes include, but are not limited to fractionation, solvent extraction, or adsorption.

One or more of the fractions 50, 55, 60, 65, 70 can be further processed, as desired. For example, as illustrated in FIG. 1, the fraction 60 can be sent to one or more hydrocarbon conversion zones 75. Suitable hydrocarbon conversion zones 75 include, but are not limited to, hydrotreating zones, hydrocracking zones, fluid catalytic cracking zones, alkylation zones, transalkylation zones, light cycle oil process zones, and the like.

As shown in FIG. 1, the fraction 60 is routed to a hydrotreating zone. Hydrotreating is a process in which hydrogen gas 80 is contacted with a hydrocarbon stream in the presence of suitable catalysts which are primarily active for the removal of heteroatoms, such as organic sulfur, nitrogen, and oxygen, and metals from the hydrocarbon feedstock. In hydrotreating, hydrocarbons with double and triple bonds may be saturated. Aromatics may also be saturated. The hydrotreating reaction conditions include a temperature of about 290° C. (550° F.) to about 455° C. (850° F.), a hydrogen partial pressure of about 4,100 kPa (595 psig) to about 17,250 kPa (2,502 psig), a liquid hourly space velocity of about 0.5 $hr^{-1}$ to about 4 $hr^{-1}$, and a hydrogen rate of about 168 to about 1,011 $Nm^3/m^3$ oil (1,000-6,000 scf/bbl). The hydrotreating catalysts include at least one Group VIII metal, preferably iron, cobalt and nickel, and at least one Group VI metal, preferably molybdenum and tungsten, on a high surface area support material, preferably alumina. Other hydrotreating catalysts include zeolitic catalysts, as well as noble metal catalysts where the noble metal is selected from palladium and platinum. In particular, the hydrotreating catalyst preferably includes a zeolitic hydrotreating catalyst comprising one or more of nickel, molybdenum, cobalt, and tungsten.

After hydrotreating, the hydrotreated stream 85 is routed to a hydrocracking zone 90. Hydrocracking is a process in which hydrocarbons crack in the presence of hydrogen and one or more hydrocracking catalysts to lower molecular weight hydrocarbons. Typical hydrocracking conditions may include a temperature of about 290° C. (550° F.) to about 468° C. (875° F.), a hydrogen partial pressure of about 1,350 kPa (196 psig) to about 17,250 kPa (2502 psig), a liquid hourly space velocity (LHSV) of about 0.5 to about 2.5 $hr^{-1}$, and a hydrogen rate of about 421 to about 2,527 $Nm^3/m^3$ oil (2,500-15,000 scf/bbl). The hydrocracking catalysts include, for example, amorphous silica-alumina bases or low-level zeolite bases combined with one or more Group VIII or Group VIB metal hydrogenating components. Alternatively, the hydrocracking catalysts may include crystalline zeolite cracking base upon which is deposited a Group VIII metal hydrogenating component. Additional hydrogenating components may be selected from Group VIB for incorporation with the zeolite base.

In particular, the hydrocracking process preferably further saturates at least a portion of remaining multi-ring aromatic compounds. Additionally, the cracking phenomenon of the hydrocracking process causes at least one ring of a portion of multi-ring aromatic compounds contained in the hydrotreated stream 85 to be "opened," thereby breaking the ring and forming a single-ring aromatic compound.

The hydrocracking catalyst is preferably regenerated in situ. This can be accomplished by forming the hydrocracking zone 90 as a fluidized bed reactor, including introducing a fluid 95 such as steam to a reactor bed containing a granular hydrocracking catalyst material. The fluid 95 is introduced near a bottom of the reactor, and flows upward through the granular catalyst. Increasing the velocity of the steam causes aerodynamic drag forces imparted by the steam to counteract the gravitational forces, causing the bed to expand in volume as the particles move away from each other. When the steam velocity reaches a critical value at which the upward drag forces produced by the steam are equal to the downward gravitational forces exerted on the granular catalyst, the catalyst granules become suspended within the fluid. At this critical value, the bed is said to be fluidized and will exhibit fluidic behavior. The fluidization allows for substantially continuous withdrawal of spent catalyst and introduction of active (i.e. fresh and/or regenerated) catalyst. Alternatively, the hydrocracking zone 90 may be operated as a swing bed reactor. That is, the hydrocracking zone 90 may include multiple reactor beds, each containing hydrocracking catalyst. When the hydrotreated stream 85 is introduced to the hydrocracking zone 90, the stream is selectively routed to a first of the beds to undergo hydrocracking as discussed above. The hydrocracking process causes the catalyst contained in the first bed to become "spent" by depositing coke onto the catalyst, causing the catalyst to become less active. Once the catalyst in the first bed is sufficiently spent, the incoming hydrotreated stream is selectively routed to a second bed containing active catalyst, and the spent catalyst in the first bed undergoes regeneration as is known in the art. Similarly, when catalyst in the second bed is sufficiently spent, the incoming hydrotreated stream is selectively rerouted to the first bed containing active catalyst, and the spent catalyst in the second bed undergoes regeneration. In both cases, the hydrocracking zone 90 can be operated substantially continuously.

The hydrocracked stream 100 is routed to a dealkylating zone 105 to selectively dealkylate the single ring hydrocarbon compounds. The selective dealkylation preferably removes alkyl groups containing two or more carbon atoms, while preserving alkyl groups having a single carbon atom (i.e., methyl groups). The selective dealkylation is performed by contacting the hydrocracked stream 100 with a dealkylation catalyst, the dealkylation catalyst being a monometallic catalyst comprising a strong acid zeolite such as a mordenite-type zeolite, or heteropolyacid. The catalyst preferably removes substantially all alkyl groups containing two or more carbon atoms, while removing less than 10% of alkyl groups having only a one carbon and three hydrogen atoms. Removing the relatively long alkyl groups from the single-ring aromatics provides a product stream 115 rich in single ring aromatics that may contain methyl groups.

The product stream 115 may be subject to additional downstream processes as is known in the art. For example, additional separation or distillation processes, isomerization processes, transalkylation processes, alkylation processes, and the like may be desirable to maximize particular alkylaromatic products.

Transalkylation is a chemical reaction resulting in transfer of an alkyl group from one organic compound to another. Catalysts, particularly zeolite catalysts, are often used to effect the reaction. If desired, the transalkylation catalyst may be metal stabilized using a noble metal or base metal, and may contain suitable binder or matrix material such as inorganic oxides and other suitable materials. In a transalkylation process, a polyalkylaromatic hydrocarbon feed and an aromatic hydrocarbon feed are provided to a transalkylation reaction zone. The feed is usually heated to reaction temperature and then passed through a reaction zone, which may comprise one or more individual reactors. Passage of the combined feed through the reaction zone produces an effluent stream comprising unconverted feed and product monoalkylated hydrocarbons. This effluent is normally cooled and passed to a stripping column in which substantially all $C_5$ and lighter hydrocarbons present in the effluent are concentrated into an overhead stream and removed from the process. An aromatics-rich stream is recovered as net stripper bottoms, which is referred to as the transalkylation effluent.

The transalkylation reaction can be effected in contact with a catalytic composite in any conventional or otherwise convenient manner and may comprise a batch or continuous type of operation, with a continuous operation being preferred. The transalkylation catalyst is usefully disposed as a fixed bed in a reaction zone of a vertical tubular reactor, with the alkylaromatic feed stock charged through the bed in an upflow or downflow manner. The transalkylation zone normally operates at conditions including a temperature in the range of about 130° C. to about 540° C. The transalkylation zone is typically operated at moderately elevated pressures broadly ranging from about 100 kPa to about 10 MPa absolute. The transalkylation reaction can be effected over a wide range of space velocities. That is, volume of charge per volume of catalyst per hour; weight hourly space velocity (WHSV) generally is in the range of from about 0.1 to about 30 $hr^{-1}$. The catalyst is typically selected to have relatively high stability at a high activity level.

Alkylation is typically used to combine light olefins, for example mixtures of alkenes such as propylene and butylene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When using benzene, the product resulting from the alkylation reaction is an alkylbenzene (e.g. toluene, xylenes, ethylbenzene, etc.). For isobutane alkylation, typically, the reactants are mixed in the presence of a strong acid catalyst, such as sulfuric acid or hydrofluoric acid. The alkylation reaction is carried out at mild temperatures, and is typically a two-phase reaction. Because the reaction is exothermic, cooling is needed. Depending on the catalyst used, normal refinery cooling water provides sufficient cooling. Alternatively, a chilled cooling medium can be provided to cool the reaction. The catalyst protonates the alkenes to produce reactive carbocations which alkylate the isobutane reactant, thus forming branched chain paraffins from isobutane. Aromatic alkylation is generally now conducted with solid acid catalysts including zeolites or amorphous silica-aluminas.

The alkylation reaction zone is maintained at a pressure sufficient to maintain the reactants in liquid phase. For a hydrofluoric acid catalyst, a general range of operating pressures is from about 200 to about 7,100 kPa absolute. The temperature range covered by this set of conditions is from about −20° C. to about 200° C. For at least alkylation of aromatic compounds, the temperature range is about from 100° C. to about 200° C. at the pressure range of about 200 to about 7,100 kPa.

In some processes, all or a portion of the coal feed 10 is mixed with oxygen 120 and steam 125 and reacted under heat and pressure in the gasification zone 20 to form syngas 130, which is a mixture of carbon monoxide and hydrogen. The syngas 130 can be further processed using the Fischer-Tropsch reaction to produce gasoline or using the water-gas shift reaction to produce more hydrogen.

Figure 2:
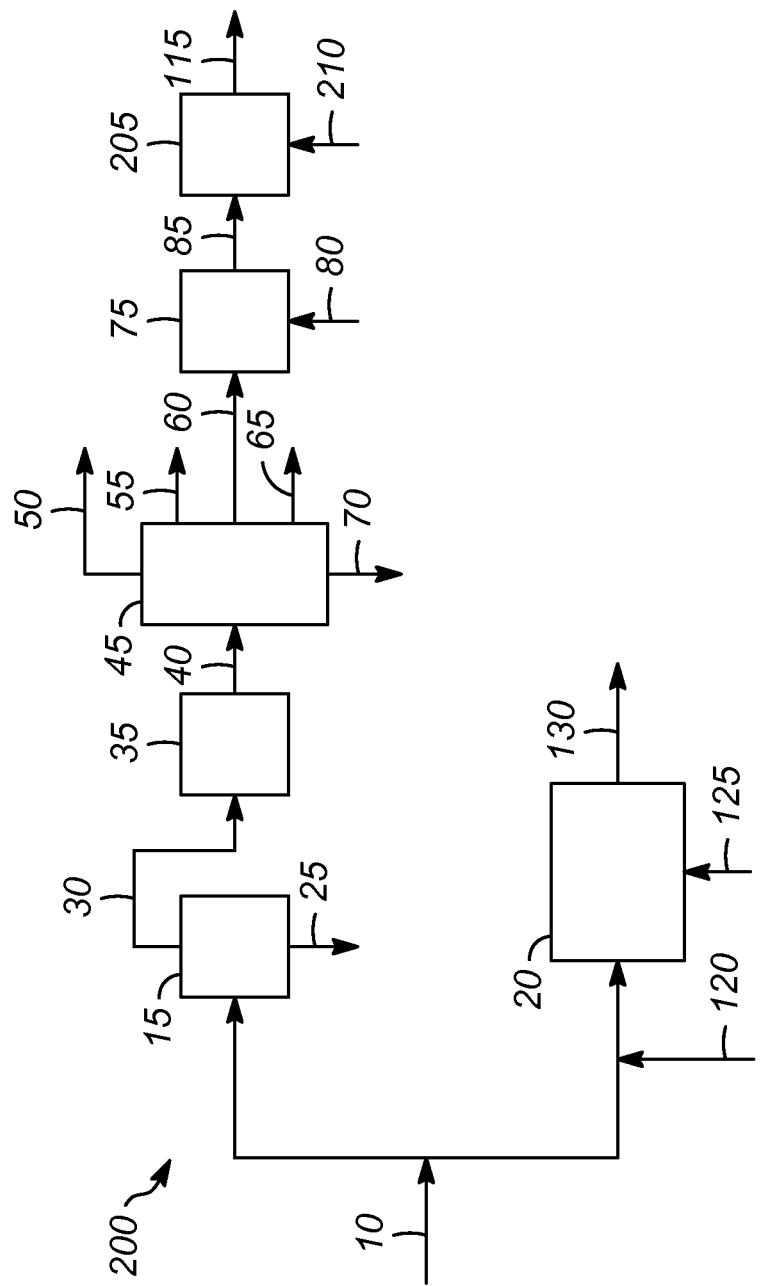
FIG. 2 is an illustration of another embodiment of the process of the present invention for dealkylating aromatic compounds.

In another embodiment as shown in FIG. 2, a process for selectively dealkylating aromatic hydrocarbons is generally designated 200. In the process 200, hydrocracking and dealkylating are performed in a combined hydrocracking and dealkylation zone 205. Other portions of the process 200 are substantially similar to the process 5 in FIG. 1, and are designated using identical reference numbers to aid understanding.

A hydrotreated stream 85 is routed from a hydrocracking zone 75 to a combined hydrocracking and dealkylation zone 205. The combined zone 205 performs hydrocracking and dealkylation substantially contemporaneously. Hydrocracking is a process in which hydrocarbons crack in the presence of hydrogen and one or more catalysts to lower molecular weight hydrocarbons. Typical hydrocracking conditions may include a temperature of about 290° C. (550° F.) to about 468° C. (875° F.), a hydrogen partial pressure of about 1350 kPa (196 psig) to about 8275 kPa (1200 psig), a liquid hourly space velocity (LHSV) of about 1.0 to less than about 2.5 $hr^{-1}$, and a hydrogen rate of about 421 to about 2,527 $Nm^3/m^3$ oil (2,500 to 15,000 scf/bbl). The catalysts are catalysts suitable for both cracking and dealkylation, and include, for example, crystalline zeolite cracking base, such as a mordenite-type zeolite or a heteropolyacid, upon which is deposited a Group VIII metal hydrogenating component. Additional hydrogenating components may be selected from Group VIB for incorporation with the zeolite base.

In particular, the hydrocracking process preferably further saturates at least a portion of remaining multi-ring aromatic compounds. Additionally, the cracking phenomenon of the hydrocracking process causes at least one ring of a portion of multi-ring aromatic compounds contained in the hydrotreated stream 85 to be "opened," thereby breaking the ring and forming a single-ring aromatic compound.

Additionally, the catalyst causes single ring aromatic compounds present to be selectively dealkylated. The selective dealkylation preferably removes alkyl groups containing two or more carbon atoms, while preserving alkyl groups having a single carbon atom. That is, contact with the catalyst preferably removes substantially all alkyl groups containing two or more carbon atoms, while removing less than 10% of alkyl groups having a single carbon atom. Removing the relatively long alkyl groups from the single-ring aromatics provides a product stream 115 rich in single ring aromatics that may contain methyl groups.

The catalyst is preferably regenerated in situ, using either a fluidized bed or a swing bed setup as described above. This allows the hydrocracking and dealkylation zone 205 to operate substantially continuously.

The product stream 115 may be subject to additional downstream processes as is known in the art. For example, additional separation or distillation processes, isomerization processes, transalkylation processes, alkylation processes, and the like may be desirable to maximize particular alkylaromatic products.

While exemplary embodiments have been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The invention claimed is:

1. A process for selectively dealkylating aromatic compounds, comprising:
    pyrolyzing a coal feed stream into a coke stream and a coal tar stream comprising aromatic compounds;
    hydrotreating the coal tar stream in the presence of a hydrotreating catalyst comprising at least one of group VIII metals, and at least one group VI metals to reduce a concentration of one or more of organic sulfur, nitrogen, and oxygen in the coal tar stream, and to hydrogenate at least a portion of the aromatic compounds to naphthenes in the coal tar stream to produce a hydrotreated coal tar stream;
    hydrocracking the hydrotreated coal tar stream in the presence of a catalyst comprising amorphous silica-alumina bases or low-level zeolite bases combined with one or more Group VIII or Group VIB metal hydrogenating components to further hydrogenate the aromatic compounds and to crack at least one ring of multi-ring aromatic compounds to form single-ring aromatic compounds; and
    dealkylating the single-ring aromatic compounds in the presence of a dealkylating catalyst, the dealkylating catalyst being a monometallic catalyst comprising at least one of a strong acid zeolite and a heteropolyacid to remove substantially all alkyl groups containing two or more carbon atoms, while removing less than 10% of alkyl groups having only one carbon and three hydrogen atoms.

2. The process of claim 1, wherein group VI and group VIII metals of the hydrotreating catalyst include nickel, molybdenum, cobalt, and tungsten.

3. The process of claim 2 wherein hydrotreating the coal tar stream takes place at a hydrogen partial pressure in the range of about 4,100 kPa (595 psi) to about 17,250 kPa (2,502 psi).

4. The process of claim 1 wherein said hydrocracking takes place at a temperature in the range of about 300° C. to about 450° C. and at a hydrogen partial pressure in the range of about 1,350 kPa (196 psi) to about 17,250 kPa (2,502 psi).

5. The process of claim 1 wherein said strong acid comprises one or more of a mordenite-type zeolite and a heteropolyacid.

6. The process of claim 1 wherein hydrocracking the hydrotreated coal tar stream comprises introducing a hydrocracking catalyst and the hydrotreated hydrocarbon stream into a hydrocracking zone including a fluidized bed.

7. The process of claim 1 wherein hydrocracking the hydrotreated coal tar stream comprises introducing the hydrotreated hydrocarbon stream to a hydrocracking zone including a first reactor bed and a second reactor bed, wherein both the first reactor bed and the second reactor bed contain a hydrocracking catalyst, wherein the hydrotreated hydrocarbon stream is selectively routed to one of the first reactor bed and the second reactor bed for hydrocracking, and wherein the other of the first reactor bed and the second reactor bed undergoes regeneration processing to regenerate the hydrocracking catalyst.

\* \* \* \* \*